(12) United States Patent
Matranga et al.

(10) Patent No.: US 8,986,511 B1
(45) Date of Patent: Mar. 24, 2015

(54) VISIBLE LIGHT PHOTOREDUCTION OF $CO_2$ USING HETEROSTRUCTURED CATALYSTS

(75) Inventors: Christopher Matranga, Pittsburgh, PA (US); Robert L. Thompson, Pittsburgh, PA (US); Congjun Wang, Bethel Park, PA (US)

(73) Assignee: U.S. Department of Energy, Washington, DC (US)

( * ) Notice: Subject to any disclaimer, the term of this patent is extended or adjusted under 35 U.S.C. 154(b) by 460 days.

(21) Appl. No.: 12/903,282

(22) Filed: Oct. 13, 2010

Related U.S. Application Data

(60) Provisional application No. 60/251,388, filed on Oct. 14, 2009.

(51) Int. Cl.
    *B01J 19/08* (2006.01)
    *C07C 1/12* (2006.01)
    *C07C 9/04* (2006.01)

(52) U.S. Cl.
    USPC .................................. 204/157.15; 204/157.52

(58) Field of Classification Search
    USPC ............ 204/157.52, 157.47, 157.15; 205/340
    See application file for complete search history.

(56) References Cited

U.S. PATENT DOCUMENTS

| | | | | |
|---|---|---|---|---|
| 4,167,461 A | * | 9/1979 | Dickson et al. | 205/340 |
| 4,240,882 A | * | 12/1980 | Ang et al. | 205/340 |
| 4,381,978 A | * | 5/1983 | Gratzel et al. | 205/340 |
| 4,427,749 A | * | 1/1984 | Graetzel et al. | 205/340 |
| 4,437,954 A | * | 3/1984 | Sammells et al. | 205/340 |
| 4,443,311 A | * | 4/1984 | Lichtin et al. | 204/157.82 |
| 4,451,342 A | * | 5/1984 | Lichtin et al. | 204/157.15 |
| 4,484,992 A | * | 11/1984 | Buhler et al. | 204/157.52 |
| 4,523,981 A | * | 6/1985 | Ang et al. | 205/340 |
| 4,623,437 A | * | 11/1986 | Visca et al. | 204/157.47 |
| 4,889,604 A | * | 12/1989 | Khan et al. | 204/157.52 |
| 5,022,970 A | * | 6/1991 | Cook et al. | 205/340 |
| 6,916,414 B2 | * | 7/2005 | Dolan | 205/316 |
| 7,042,029 B2 | | 5/2006 | Graetzel et al. | |
| 7,169,733 B2 | * | 1/2007 | Wang et al. | 502/300 |
| 7,605,062 B2 | * | 10/2009 | Kahen | 977/892 |

(Continued)

OTHER PUBLICATIONS

Levy, "Photochemistry of Nanostructured Materials for Energy Applications," J. of Electroceramics vol. 1, issue 3, pp. 239-272 (1997).*

(Continued)

*Primary Examiner* — Colleen M Raphael
(74) *Attorney, Agent, or Firm* — James B. Potts; Brian J. Lally; John T. Lucas

(57) ABSTRACT

The method provides for use of sensitized photocatalyst for the photocatalytic reduction of $CO_2$ under visible light illumination. The photosensitized catalyst is comprised of a wide band gap semiconductor material, a transition metal co-catalyst, and a semiconductor sensitizer. The semiconductor sensitizer is photoexcited by visible light and forms a Type II band alignment with the wide band gap semiconductor material. The wide band gap semiconductor material and the semiconductor sensitizer may be a plurality of particles, and the particle diameters may be selected to accomplish desired band widths and optimize charge injection under visible light illumination by utilizing quantum size effects. In a particular embodiment, $CO_2$ is reduced under visible light illumination using a CdSe/Pt/TiO2 sensitized photocatalyst with $H_2O$ as a hydrogen source.

16 Claims, 5 Drawing Sheets

(56) References Cited

U.S. PATENT DOCUMENTS

| | | | |
|---|---|---|---|
| 8,216,436 B2* | 7/2012 | Wang et al. | 204/248 |
| 2006/0140827 A1* | 6/2006 | Cheng et al. | 422/186 |
| 2006/0210798 A1* | 9/2006 | Burda | 977/906 |
| 2006/0283701 A1* | 12/2006 | Li et al. | 204/157.52 |
| 2007/0039814 A1* | 2/2007 | Maggard | 204/157.15 |
| 2008/0223713 A1* | 9/2008 | Xu et al. | 204/157.15 |
| 2009/0026063 A1* | 1/2009 | Skiles et al. | 204/157.3 |
| 2009/0321244 A1* | 12/2009 | Smith et al. | 204/157.52 |
| 2010/0133110 A1* | 6/2010 | Nocera et al. | 205/340 |
| 2010/0155218 A1* | 6/2010 | Vogt et al. | 204/157.15 |
| 2010/0213046 A1* | 8/2010 | Grimes et al. | 204/157.47 |
| 2010/0258446 A1* | 10/2010 | Mohapatra et al. | 205/340 |
| 2011/0056841 A1* | 3/2011 | Wehrenberg et al. | 205/340 |
| 2013/0098772 A1* | 4/2013 | Bocarsly et al. | 205/340 |

OTHER PUBLICATIONS

Adachi et al, "Photocatalytic reduction of carbon dioxide to hydrocarbon using copper-loaded titanium dioxide," Solar Energy, vol. 53, No. 2, pp. 187-190 (1994).*

Chen et al, "Photocatalysts for photocatalytic reduction of carbon dioxide," Huaxue Tongbao, vol. 66, issue 3, pp. 184-191 (Abstract only).*

Rajeshwar, "Hydrogen generation at irradiated oxide semiconductor-solution surfaces," J. Appl. Electrochem (2007) vol. 37, pp. 765-787.*

Ji et al, "Photocatalytic hydrogen production from natural seawater," J. of Photochem Photobio. A: Chemistry vol. 189 (2007), pp. 141-144.*

Carp et al, "Photoinduced reaction of carbon dioxide," Progress in Solid State Chemistry 32 (2004) pp. 33-177.*

Stroyuk et al, "Semiconductor photocatalytic systems for the production of hydrogen by the action of visible light," Theoretical and Experimental Chemistry vol. 45, No. 4, 2009.*

Shi et al, "Photocatalytic conversion of $CH_4$ and $CO_2$ to oxygenated compounds over $Cu/CdS$—$TiO_2/SiO_2$ catalyst," Catalysis Today vol. 98 (2004), pp. 505-509.*

Khan et al, "Photofixation of carbon dioxide in semiconductor particulate and microbal systems," Proce. Indian Acad. Sci. (Chem. Sci.), vol. 104, No. 6, Dec. 1992, pp. 747-752.*

Fang et al., "Sensitization of nanocrystalline $TiO_2$ electrode with quantum sized CdSe and ZnTCPc molecules," Chemical Physics Letters 270 (1997).

Jang et al., "Location and State of Pt in Platinized $CdS/TiO_2$ Photocatalysts for Hydrogen Production from Water under Visible Light," J. Phys. Chem. C 2008, 112.

Di Valentin et al., "Trends in non-metal doping of anatase $TiO_2$: B, C, N and F," Catal. Today (2011), doi: 10.1016/j.cattod.2011.11.030.

Li et al., "Photocatalytic reduction of $CO_2$ with $H_2O$ on mesoporous silica supported $Cu/TiO_2$ catalysts," Applied Catalysis B: Environmental 100, pp. 389-390 (2010).

Wang et al., "Visible Light Photoreduction of $CO_2$ Using $CdSe/Pt/TiO_2$ Heterostructured Catalysts," J. Phys. Chem. Lett. 1 (2010).

* cited by examiner

- Curve A is CH stretch band of a thin film of CdSe before 1M hydrazine in ethanol treatment.

- Curve B is CH stretch band of a thin film of CdSe after 1M hydrazine in ethanol treatment.

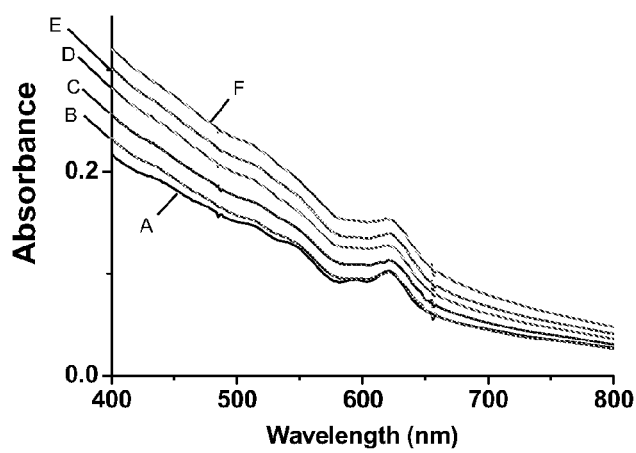

- Curve A is UV/vis spectrum of a thin film of CdSe QDs immediately before 1 M hydrazine in ethanol treatment.
- Curve B is UV/vis spectrum of a thin film of CdSe QDs immediately after 1 M hydrazine in ethanol treatment.
- Curve C is UV/vis spectrum of the thin film of CdSe QDs same film exposed to air 1 hour after 1 M hydrazine in ethanol treatment.
- Curve D is UV/vis spectrum of the thin film of CdSe QDs same film exposed to air 2 hours after 1 M hydrazine in ethanol treatment.
- Curve E is UV/vis spectrum of the thin film of CdSe QDs same film exposed to air 3 hours after 1 M hydrazine in ethanol treatment.
- Curve F is UV/vis spectrum of the thin film of CdSe QDs same film exposed to air 5 hours after 1 M hydrazine in ethanol treatment.

Fig. 4

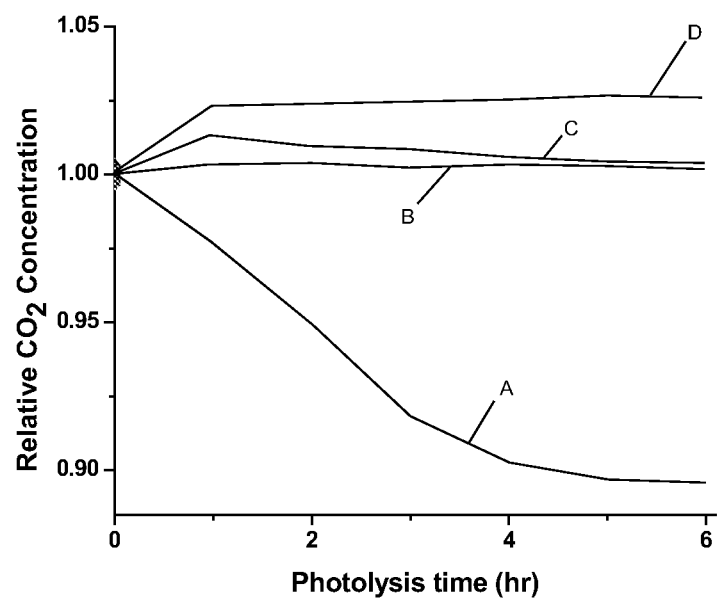

- Curve A is photocatalytic reduction of CO2 measured by IR spectroscopy using t-CdSe/Pt/TiO2 under visible light > 420 nm irradiation.
- Curve B is photocatalytic reduction of CO2 measured by IR spectroscopy using Pt/TiO2 under visible light > 420 nm irradiation.
- Curve C is photocatalytic reduction of CO2 measured by IR spectroscopy using t-CdSe/Pt/TiO2 in the dark.
- Curve D is photocatalytic reduction of CO2 measured by IR spectroscopy using t-CdSe under white light only irradiation.

Fig. 5

VISIBLE LIGHT PHOTOREDUCTION OF $CO_2$ USING HETEROSTRUCTURED CATALYSTS

RELATION TO OTHER APPLICATIONS

This patent application claims priority from provisional patent application 61/251,388, filed Oct. 14, 2009, which is hereby incorporated by reference.

GOVERNMENT INTERESTS

The United States Government has rights in this invention pursuant to the employer-employee relationship of the Government to the inventors as U.S. Department of Energy employees and site-support contractors at the National Energy Technology Laboratory.

FIELD OF THE INVENTION

One or more embodiments of the present invention relate to a sensitized photocatalyst for the photocatalytic reduction of $CO_2$ under visible light illumination. The photosensitized catalyst is comprised of a wide band gap semiconductor material, a transition metal co-catalyst, and a semiconductor sensitizer. The semiconductor sensitizer and the wide band gap semiconductor material form a Type II band alignment, and the semiconductor sensitizer has a band gap such that visible light illumination produces photoexcitation in the semiconductor sensitizer. The wide band gap semiconductor material and the semiconductor sensitizer may be a plurality of particles, and the particle diameters may be selected to accomplish desired band widths and optimize charge injection under visible light illumination by utilizing quantum size effects.

BACKGROUND

Wide band gap semiconductor materials are used as photocatalysts for degrading dilute pollutants in air and water as well as for converting $CO_2$ and $H_2O$ gases to valuable products such as hydrocarbons and $H_2$ through oxidation and reductions (redox) reactions. A particular interest is the photocatalytic reduction of $CO_2$ for the production of hydrocarbons and other valuable products using inexpensive and abundant semiconductors such as $TiO_2$ and ZnO. Such processes provide a potential means to reduce atmospheric $CO_2$, as well as providing an attractive alternative to purely chemical means of converting $CO_2$ to hydrocarbons. However, a fundamental difficulty in the widespread use of many semiconductors such as $TiO_2$ and ZnO is the requirement for ultraviolet light to drive photoexcitation. Because ultraviolet light constitutes a relatively small fraction of the solar spectrum, use of these materials for photocatalytic reduction of $CO_2$ has generally required illumination by an artificial UV light source in order to generate sufficient redox capacity. This is a parasitic load to the system as a whole, and negatively impacts the efficiency of the process. As a result, shifting the optical response of these inexpensive and abundant semiconductor materials to provide for photoexcitation in the visible spectral range while preserving the ability to facilitate specific redox reactions is the subject of significant effort. In particular, providing a methodology by which wide band gap semiconductor materials could be effectively utilized for the photocatalytic reduction of $CO_2$ as a response to visible light illumination would be of enormous benefit.

It is known that sensitization of semiconductors which respond primarily to UV light can provide a system whereby electrons excited by visible light in the sensitizer are injected into the semiconductor, and these systems have been extensively studied in applications such as solar cells and photography technology. In these systems, the band alignment of the sensitizer and the semiconductor is such that the energy level of the photoexcited electron within the sensitizer lies above the conduction band minimum of the semiconductor material. In operation, injection of electrons into the conduction band of the semiconductor material occurs upon visible light photoexcitation of the sensitizer. The bulk of the wide band gap semiconductor is used primarily for charge transport, and the arrangement further provides for charge separation in order to limit loss through recombination. Through this combination, semiconductors which respond primarily to UV light may be electronically coupled with a sensitizer, so that the response spectrum of the sensitizer-semiconductor system is extended into the visible light spectrum, and the properties of the semiconductor as an effective charge transporter can be utilized without artificial UV light sources.

Uses of these sensitizer-semiconductor configurations as redox systems driven by visible light have primarily been investigated in the degradation of dilute pollutants in air and water. Typically the underlying mechanism is described as the sensitizer injecting electrons to the semiconductor material as a result of exposure to visible light. These photoinduced electrons can transfer to molecular oxygen ($O_2$), leading to the formation of active specials, such as superoxide/hydroxide radicals and singlet oxygen in the system. The repeated attack of these active species on the organic pollutant molecules results in their ultimate decomposition to carbon dioxide, water, and simple mineral acids. See e.g., Zhang et al, "Role of oxygen active species in the photocatalytic degradation of phenol using polymer sensitized TiO2 under visible light irradiation", *Journal of Hazardous Materials* 163 (2009). These processes have been extensively investigated for the treatment of wastewaters and other pollutant-laden materials, however they rely on interaction between the injected electron and $O_2$ for the purpose of converting pollutants to less harmful $CO_2$, and do not address themselves toward the photocatalytic reduction of $CO_2$ under the environmental conditions typically reported for utilization. It would be advantageous to provide a sensitized semiconductor for the photocatalytic reduction of $CO_2$ under visible light illumination, in order to provide a potential means to reduce atmospheric $CO_2$ as well as provide a mechanism for converting $CO_2$ to hydrocarbons through more efficient use of the solar spectrum.

The use of dye sensitized platinized $TiO_2$ has also been reported for the photocatalytic reduction of $CO_2$ under illumination from a daylight lamp. See Ozcan et al., "Dye Sensitized $CO_2$ reduction over pure and platinized $TiO_2$", *Topics in Catalysis* Vol. 44, No. 4 (2007). Methane production is reported under illumination by the daylight lamp, however daylight lamps provide illumination in both the UV and visible spectrum, and it is unclear whether the $CO_2$ reduction for the production of methane reported results from UV or visible light irradiation. Additionally, dyes are known to degrade under UV light, and sensitizer-semiconductor systems such as solar cells which incorporate dyes for use under a typical solar spectrum typically include UV barriers to prolong service life. It would be advantageous to provide a methodology whereby a sensitized wide band gap semiconductor could rely solely on visible light for the photocatalytic reduction of $CO_2$ without possible reliance on included UV wavelengths and direct photoactivation of the semiconductor material, so that the sensitized semiconductor could definitively utilize the greater fraction of the solar spectrum represented by the visible light. It would be further advantageous if the sensitized semiconductor could tolerate the presence of UV light in the utilized spectrum without reliance on UV barriers for prolonged service life. Additionally, dye molecules cannot undergo impact ionization and produce quantum yields greater than one, as has been reported for quantum dot sensitized solar cells. See Fu et al, "Impact Ionization and Auger Recombination Rates in Semiconductor Quantum Dots", *J. Phys. Chem. C* 114 (2010), among others. It would be advantageous to provide a sensitized semiconductor for the photocatalytic reduction of $CO_2$ under visible light which could potentially take advantage of impact ionization and produce higher conversion efficiencies than are possible with a dye-sensitized approach.

Semiconductor materials such as $TiO_2$ have also been doped with transition metal ions and nonmetallic elements such as carbon, nitrogen, and sulfur in order to produce photocatalytic effects in the solar spectrum. Experimental and theoretical results indicate that these dopants generate localized energy levels in the $TiO_2$ just above the valence band from which visible light excitation becomes feasible. See Konstantinova et al., "Carbon-Doped Titanium Dioxide: Visible Light Photocatalysis and EPR Investigation", *CHIMIA International Journal for Chemistry*, Vol. 61, No. 12 (2007). Photocatalytic conversion of $CO_2$ and $H_2O$ to hydrocarbons has been reported using nitrogen-doped $TiO_2$ exposed to outdoor sunlight. See Varghese, et al., "High-Rate Solar Photocatalytic Conversion of CO2 and Water Vapor to Hydrocarbon Fuels", *Nano. Lett.* Vol. 9, No. 2 (2009). In these materials, the dopants are located in the lattice of the semiconductor material interstitially and/or substitutionally, in order to produce a doped semiconductor material which directly responds to visible light illumination. It would be advantageous to eliminate the interstitial and/or substitutional doping requirement and provide a sensitized semiconductor for the photocatalytic reduction of $CO_2$ under visible light, in order to simplify synthesis and take advantage of characteristics such as impact ionization which may arise.

Doped semiconductor materials have also been utilized to produce composite semiconductor materials providing for oxidation and reduction reactions under visible light. See e.g., U.S. Pat. No. 7,169,733, issued to Wang et al, issued Jan. 30, 2007. Wang produces a composite material from two doped materials, both of which photoactivate under visible light activation. In this manner, the composite material is able to provide both a hole with high oxidation potential and an electron with high reducing potential. However, the composite material relies on doping as discussed above to provide visible light excitation of both materials involved, and does not rely on a sensitizer for the injection of electrons into a wide band gap semiconductor material.

It would be advantageous to provide a method whereby the photoreduction of CO2 under visible light illumination could be accomplished using an abundant and inexpensive wide band gap semiconductor material, such as $TiO_2$ or ZnO. It would further be advantageous if visible light response was provided via electron injection from a sensitizing material responsive to visible light, in order to avoid doping requirements or other mechanisms designed to drive the wide band gap semiconductor itself into visible light photoresponse. It would be further advantageous to provide for the photoreduction of $CO_2$ in a manner that avoid sensitization using dyes, so that sensitizer degradation from the UV fraction of the solar spectrum can be avoided, and so that impact ionization and higher conversion efficiencies can potentially be realized.

Accordingly, it is an object of this disclosure to provide a method of photocatalytically reducing $CO_2$ under visible light excitation in the presence of hydrogen from a hydrogen source utilizing a sensitized photocatalyst comprised of a wide band gap semiconductor, a transition metal co-catalyst, and a semiconductor sensitizer.

It is a further object of this disclosure to photocatalytically reduce $CO_2$ under visible light excitation in the presence of hydrogen from a hydrogen source in order to produce product molecules such as hydrocarbons, $H_2$, and others.

It is a further object of this disclosure to control the composition of the product molecules based on the transition metal co-catalyst.

It is a further object of this disclosure to provide a method of photocatalytically reducing $CO_2$ utilizing a sensitized photocatalyst comprised of particles of the wide band gap semiconductor, the transition metal co-catalyst, and the semiconductor sensitizer, in order to optimize charge injection and band alignments under visible light illumination.

It is a further object of this disclosure to provide a method of photocatalytically reducing $CO_2$ under visible light illumination utilizing a sensitized photocatalyst in a $CO_2$ and $H_2O$ environment.

These and other objects, aspects, and advantages of the present disclosure will become better understood with reference to the accompanying description and claims.

SUMMARY

One or more embodiments of the present invention relates to a method for photocatalytically reducing $CO_2$ in the presence of hydrogen using a sensitized photocatalyst. The sensitized photocatalyst is comprised of a wide band gap semiconductor material in contact with a semiconductor sensitizer, and a transition metal co-catalyst loaded on the wide band gap semiconductor material. The semiconductor sensitizer has a band gap such that visible light is absorbed and photoexcitation in the semiconductor sensitizer results, driving electrons in the semiconductor from the valence band to the conduction band. The conduction band of the semiconductor sensitizer has a more negative potential than the redox potential of $CO_2$, and the semiconductor sensitizer and the wide band gap semiconductor material form a Type II band alignment, where the conduction band of the semiconductor sensitizer has a more negative potential than the conduction band of the wide band gap semiconductor material. In certain embodiments, the semiconductor sensitizer may be InP, GaAs, PbS, PbSe, ZnTe, CdS, CdSe, or CdTe, the wide band gap semiconductor material may be $TiO_2$ or ZnO, and the co-catalyst may be any transition metal.

The band gap of the semiconductor sensitizer and/or the wide band gap semiconductor material may be altered to form more advantageous Type II band alignments and photoexcitation under visible light using the quantum size effect. In a particular embodiment, the semiconductor sensitizer has diameter less than 50 nm and the wide band gap semiconductor material has a diameter less than 100 nm. In certain embodiments, the semiconductor sensitizer, the wide band gap semiconductor material, and the transition metal co-catalyst may be a plurality of particles, where individual particles in each plurality combine to produce the sensitized photocatalyst.

The method may be utilized to produce product molecules following the photocatalytic reduction of $CO_2$ with visible light illumination. In a particular embodiment, the product molecules are comprised of hydrocarbons, such as $CH_4$, $CH_3OH$, and others. The method may be utilized for production of additional product molecules, such as CO and $H_2$. The composition of the product molecules is impacted by the specific transition metal co-catalyst utilized. The hydrogen source utilized in the method may be any source providing $H^+$ atomic hydrogen. For example, the hydrogen source utilized in the method may be $H_2O$ or $H_2$. The method may further utilize a hole scavenger.

Specific results are provided for a sensitized photocatalyst comprised of CdSe and $TiO_2$ nanoparticles, using $H_2O$ as the hydrogen source.

The novel method and principles of operation are further discussed in the following description.

BRIEF DESCRIPTION OF THE DRAWINGS

FIG. 4 shows UV/vis spectrum of CdSe QDs before and after 1 M hydrazine in ethanol treatment.

FIG. 5 shows photocatalytic reduction of $CO_2$ measured by IR spectroscopy.

DETAILED DESCRIPTION

Figure 1:
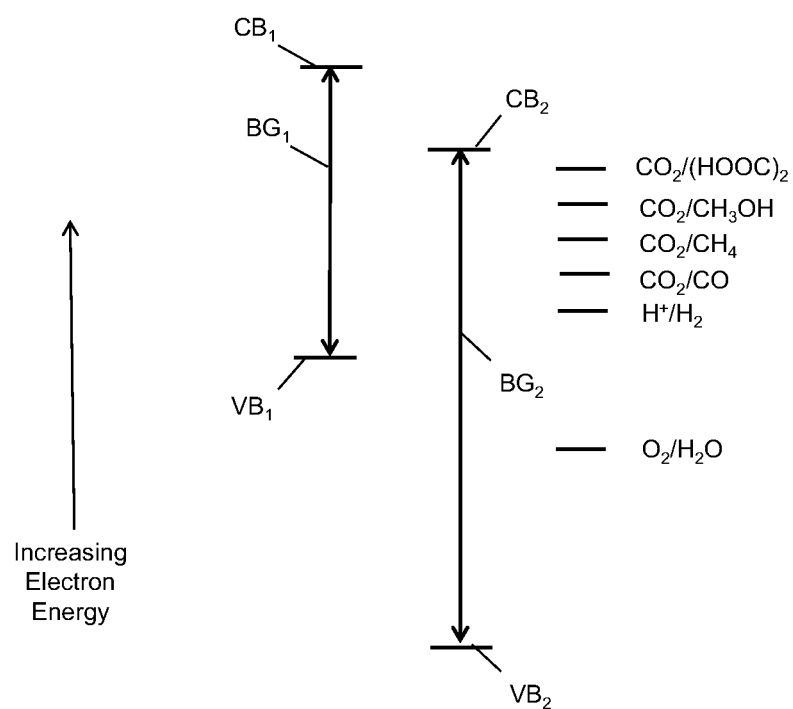
FIG. 1 shows conduction and valence bands with Type II alignment in a sensitized semiconductor system.

The disclosure herein provides a method for photocatalytically reducing $CO_2$ in the presence of hydrogen using a sensitized photocatalyst. The sensitized photocatalyst is comprised of a wide band gap semiconductor material in contact with a semiconductor sensitizer, and a transition metal co-catalyst loaded on the wide band gap semiconductor material. In order to affect photocatalytic reduction of $CO_2$ using visible light, the semiconductor sensitizer has a band gap such that visible light is absorbed and photoexcitation in the semiconductor sensitizer results, driving electrons in the semiconductor from the valence band to the conduction band. The conduction band of the semiconductor sensitizer has a more negative potential than the redox potential of $CO_2$, and semiconductor sensitizer and the wide band gap semiconductor material form a Type II band alignment, where the conduction band of the semiconductor sensitizer has a more negative potential than the conduction band of the wide band gap semiconductor material.

Within this disclosure, "visible light" means light having a wavelength λ greater than 420 nm.

Within this disclosure, "visible light illumination" means illumination by light comprised at least partially of visible light, with the balance of the illumination, if any, consisting of light having wavelengths outside the visible light range, for example, UV light. For example, exposure to sunlight comprised of visible and UV light constitutes visible light illumination within this disclosure.

Within this disclosure, "reduction" means the gain of electrons or a decrease in oxidation state by a molecule, atom, or ion. Similarly, "oxidation" means the loss of electrons or an increase in oxidation state by a molecule, atom, or ion.

Within this disclosure, "semiconductor" means a metallic material comprised of one or more metals where the metallic material has an electrical conductivity between a conductor and an insulator, generally between about $10^3$ to about $10^{-9}$ $ohm^{-1} cm^{-1}$. The term "binary semiconductor" means a semiconductor consisting of two elements.

Within this disclosure, "wide band gap semiconductor" means a semiconductor material having a conduction band energy more negative than the reduction potential of at least one $CO_2$ reduction reaction, for example, the reduction reactions of $CO_2$ to $(HOOC)_2$, $CH_3OH$, $CH_4$, or CO, among others. Wide band gap semiconductors include but are not limited to $TiO_2$ and ZnO.

Within this disclosure, "semiconductor sensitizer" means a binary semiconductor which is photoexcited by visible light. Semiconductor sensitizers include but are not limited to InP, GaAs, PbS, PbSe, ZnTe, CdS, CdSe, and CdTe.

Within this disclosure, "Type II band alignment" means a band alignment between a first semiconductor and a second semiconductor, where the conduction band of the first semiconductor has a more negative potential than the conduction band of the second semiconductor, and where the valence band of the first semiconductor has a more negative potential than the valence band of the second semiconductor.

The method provides for utilizing a sensitized photocatalyst for photocatalytically reducing $CO_2$ under visible light illumination. The sensitized photocatalyst utilizes the Type II band alignment and the transition metal co-catalyst to enhance the photoreduction activity. In operation, the sensitized photocatalyst is placed in contact with $CO_2$ and hydrogen from a hydrogen source and exposed to visible light illumination. The sensitized photocatalyst catalyzes the photoreduction of $CO_2$ in the presence of the hydrogen to produce products such as $CH_4$, $CH_3OH$, $H_2$, CO, and other hydrocarbons. The activity of the system is manipulated so that no ultraviolet light is needed for the photoreduction, although ultraviolet light may be present within the illumination utilized. The hydrogen source may be $H_2O$, $H_2$, or other appropriate sources which produce atomic hydrogen known in the art. The results represent a significant new finding for the photocatalytic reuse of $CO_2$, namely that the lower energy tails of the solar spectrum can be utilized for this application. As such, the results demonstrate a first step towards making more efficient photocatalysts for $CO_2$ capture and reuse.

The band alignment is illustrated at FIG. 1. At FIG. 1, a semiconductor sensitizer has conduction band $CB_1$, valence band $VB_1$, and a band gap $BG_1$ between $CB_1$ and $VB_1$. A wide band gap semiconductor has conduction band $CB_2$, valence band $VB_2$, and a band gap $BG_2$ between $CB_2$ and $VB_2$. The direction of increasing electron energy represented by the bands is as indicated at FIG. 1, where more negative potentials indicate increasing electron energy in a respective band. The band gap $BG_1$ of the semiconductor sensitizer is such that visible light may be absorbed and photoexcitation occurs, resulting in photoexcited electrons shifting from the valence band $VB_1$ to the conduction band $CB_1$. Conduction band $CB_1$ has a more negative potential than conduction band $CB_2$. Additionally, the conduction band $CB_2$ represents a more negative potential than the redox potential of at least one $CO_2$ reduction reaction, such as the reduction reactions of $CO_2$ to $(HOOC)_2$, $CH_3OH$, $CH_4$, or CO, as illustrated with reference to the increasing electron energy at FIG. 1. The heterojunction between the semiconductor sensitizer and the wide band gap semiconductor material thus forms a type II band alignment, where the conduction band of the semiconductor sensitizer has a more negative potential than the conduction band of the wide band gap semiconductor material.

In an embodiment, the semiconductor sensitizer may be InP, GaAs, PbS, PbSe, ZnTe, CdS, CdSe, or CdTe. The semiconductor sensitizer is preferably a binary semiconductor having a direct band gap. The wide band gap semiconductor material is preferably a semiconductor material having a band gap between the valence band and the conduction band larger than 1 eV, more preferably larger than 2 eV. In a particular embodiment, the wide band gap semiconductor material may be $TiO_2$ or ZnO. Further, the wide band gap semiconductor material may be comprised of more than a single homogenous material, provided contact between the semiconductor sensitizer and the wide band gap semiconductor material form a type II band alignment, and provided that the conduction band of the wide band gap semiconductor represents a more negative potential than the redox potential of at least one $CO_2$ reduction reaction.

The sensitized photocatalyst is further comprised of a transition metal co-catalyst loaded on the wide band gap semiconductor material. Within this disclosure, when the co-catalyst is loaded on the wide band gap semiconductor material, this indicates that the wide band gap semiconductor material acts as a support for the co-catalyst. When the co-catalyst is loaded on the wide band gap semiconductor material, the co-catalyst does not substitute into the lattice of the wide band gap semiconductor material, except to the extent that a preparation method may result in incidental substitutions. The transition metal co-catalyst may be any transition metal as defined by the International Union of Pure and Applied Chemistry (IUPAC). In a particular embodiment the semiconductor sensitizer is CdSe, the wide band gap semiconductor material is $TiO_2$, and the transition metal co-catalyst is Pt.

It is known that $CO_2$ may be reduced to CO and $O_2$ on Pt/TiO2 samples irradiated by UV light. Without being bound by theory, it is possible that upon irradiation of the semiconductor sensitizer by visible light, injected electrons act to reduce $CO_2$ in the presence of the co-catalyst loaded wide band gap semiconductor via the reaction $CO_2+2e^- \rightarrow CO+\frac{1}{2}O_2$. The CO thus formed would react with atomic hydrogen to form hydrocarbons through the reaction $CO+6e^-+6H^+ \rightarrow CH_4+H_2O$. However, these mechanics are not well understood, and the possible reactions involved in the photocatalytic reduction of $CO_2$ on the sensitized photocatalyst utilized within this disclosure are not intended to be limiting. Within this method, it is only necessary that the sensitized photocatalyst described within this disclosure be exposed to $CO_2$ and atomic hydrogen from a hydrogen source under visible light illumination.

The band gap of the semiconductor sensitizer and/or the wide band gap semiconductor material may be altered to form more advantageous Type II band alignments and photoexcitation under visible light using the quantum size effect, as is known in the art. See e.g., A. Henglein, "Q-particles: Size quantization effects in colloidal semiconductors", *Progr Colloid & Polymer Sci* 73:1-4 (1987), among others. In a particular embodiment, the semiconductor sensitizer, the wide band gap semiconductor material, and the transition metal co-catalyst are a plurality of particles, where individual particles in each plurality combine to produce the sensitized photocatalyst. In this embodiment, the sensitized photocatalyst is formed when semiconductor sensitizer particles contact the co-catalyst loaded wide band gap semiconductor particles. This approach provides for advantages in synthesis as well as allowing for sensitized photocatalyst tuning through the quantum size effects previously referenced.

Additionally, when the semiconductor sensitizer, the wide band gap semiconductor material, and the transition metal co-catalyst are a plurality of particles, the diameter of the semiconductor sensitizer particles and the wide band gap semiconductor particles may be selected in order to produce an optimum charge injection from the semiconductor sensitizer particles to the wide band gap semiconductor particles on exposure to visible light illumination. Similarly, the diameter of the semiconductor sensitizer particles may be selected so that quantum confinement shifts the conduction band of the semiconductor sensitizer to higher energies to facilitate charge injection into the wide band gap semiconductor material, as is known in the art. See e.g., Fang et al, "Sensitization of nanocrystalline TiO2 electrode with quantum sized CdSe and ZnTCPc molecules", *Chemical Physics Letters* 270 (1997), among others. In an embodiment, a semiconductor sensitizer particle diameter is less than 10 nm and a wide band gap semiconductor particle diameter is less than 50 nm. In another embodiment, the semiconductor sensitizer is comprised of CdSe particles approximately 2.5-6 nm in diameter and the wide band gap semiconductor is comprised of $TiO_2$ particles approximately 25 nm in diameter. Preferably, the sensitizing particles are substantially uniformly distributed and in close/direct contact with the semiconductor particles. It is known that outer-sphere electron transfer rates are strongly distance-dependent, and contact among small particles as described can facilitate the process. Sensitizing particle uniformity may be evaluated using scanning electron microscopy (SEM) images and EDS analysis, as is known in the art.

Within the method disclosed, the sensitized photocatalyst comprised of the semiconductor sensitizer, the wide band gap semiconductor material, and the transition metal co-catalyst is exposed to visible light illumination and atomic hydrogen $H^+$ from a hydrogen source, and some portion of the $CO_2$ is photocatalytically reduced. Within this method, visible light indicates light having a wavelength $\lambda$ greater than 420 nm. However, when the method specifies exposure to visible light illumination, this is not intended to indicate that all illuminating light has a wavelength $\lambda$ greater than 420 nm. The illuminating light may be comprised of visible light as defined herein as well as light having wavelengths outside the specified visible light range, such as UV light. Within this disclosure, it is only necessary that the visible light illumination be comprised at least partially of light having a wavelength $\lambda$ greater than 420 nm. For example, exposure to sunlight comprised of visible and UV light constitutes visible light illumination within this disclosure.

In an embodiment of the method, close contact between the semiconductor sensitizer and the wide band gap semiconductor material is enhanced through removal of ligands on the semiconductor sensitizer. As is known in the art, strong electronic coupling and efficient electron injection requires a favorable link between the semiconductor sensitizer and the wide band gap semiconductor material. However, nanodimensioned sensitizer particles do not always adhere strongly to particles of wide band gap semiconductors, and linker molecules may be utilized to provide linkage through present functional groups. The presence of these linker molecules can adversely impact the photocatalyst properties. See e.g., Liu et al., "Preparation and Photoelectrochemical Properties of CdSe/TiO2 Hybrid Mesoporous Structures", *J. Phys. Chem. Lett.* 1 (2010). In a particular embodiment utilizing CdSe particles approximately 2.5 and 6 nm in diameter, the CdSe particles were treated with a hydrazine chemical treatment to remove surface ligands and improve the electronic coupling with $TiO_2$. Additionally, removal of surface ligands may be accomplished through thermal annealing or other suitable methods known in the art.

The method may be utilized to produce product molecules following the photocatalytic reduction of $CO_2$ with visible light illumination. In a particular embodiment, the product molecules are comprised of hydrocarbons, such as $CH_4$, $CH_3OH$, and others. The method may be utilized for production of additional product molecules, such as CO and $H_2$. The composition of the product molecules is impacted by the specific transition metal co-catalyst utilized. As a result, production of specific product molecules may be enhanced through advantageous selection of the transition metal co-catalyst. For example, in an embodiment utilizing a sensitized photocatalyst comprised of CdSe particles and $TiO_2$ particles, use of Pt as the co-catalyst results in product molecules comprised largely of $CH_4$, where use of Fe as the co-catalyst results in product molecules comprised largely of $H_2$.

The hydrogen source utilized in the method may be any source providing $H^+$ atomic hydrogen. For example, the hydrogen source utilized in the method may be $H_2O$ or $H_2$ under conditions where $H^+$ atomic hydrogen is produced. The method may further utilize a hole scavenger. In a particular embodiment utilizing a CdSe/Pt/TiO2 sensitized photocatalyst with $H_2O$ as a hydrogen source, $Na_2S$ present in the $H_2O$ is utilized as a hole scavenger.

The method disclosed provides for utilizing the sensitized photocatalyst for the photocatalytically reduction of $CO_2$ under visible light illumination. The Type II band alignment and the transition metal co-catalyst facilitate the photoreduction activity. The sensitized photocatalyst may be comprised of a plurality of semiconductor sensitizer particles, co-catalyst particles, and wide band gap semiconductor material particles, and the diameter of the particles may be selected in order to manipulate quantum confinement effects and provide for efficient $CO_2$ reduction. When the sensitized photocatalyst is placed in contact with $CO_2$ and atomic hydrogen from a hydrogen source and exposed to visible light illumination, the sensitized photocatalyst catalyzes the photoreduction of $CO_2$ in the presence of the hydrogen to produce products such as $CH_4$, $CH_3OH$, $H_2$, CO, and other hydrocarbons. The activity of the system is manipulated so that no ultraviolet light is needed for the photoreduction, although ultraviolet light may be present within the illumination utilized. The hydrogen source may be $H_2O$, $H_2$, or other appropriate sources which produce atomic hydrogen as known in the art. The results represent a significant new finding for the photocatalytic reuse of $CO_2$, namely that the lower energy tails of the solar spectrum can be utilized for this application. As such, the results demonstrate a first step towards making more efficient photocatalysts for $CO_2$ capture and reuse

DETAILED DESCRIPTION OF AN EMBODIMENT

In an exemplary embodiment, a sensitized photocatalyst is comprised of a CdSe nanodimensioned semiconductor sensitizer and a $TiO_2$ wide band gap semiconductor material. In order to enhance the photoreduction activity, various transition metal co-catalysts such as Pt were incorporated onto the $TiO_2$. The hydrogen source utilized was $H_2O$.

A CdSe/Pt/$TiO_2$ sensitized photocatalyst was synthesized using commercial P25 $TiO_2$ nanoparticles and CdSe QDs. The Pt was incorporated by wet impregnation methods onto the $TiO_2$. See Jang et al, *J. Phys. Chem. C* 2008, 112, 172000-17205. Two sizes of CdSe QDs (2.5 nm and 6 nm diameter) were then mixed with the Pt/$TiO_2$. One set of samples were thermally annealed in an inert atmosphere to desorb the organic capping molecules on the CdSe QDs and are referred to as t-CdSe/Pt/$TiO_2$. See Lee et al, *Appl. Phys. Lett.* 2007, 91, 113104. Likewise, the caps were also removed using a chemical hydrazine treatment of the CdSe QDs prior to mixing with $TiO_2$ and are referred to as c-CdSe/Pt/$TiO_2$. See Law et al, *J. Am. Chem. Soc.* 2008, 130, 5974-5985. Approximately 300 mg of the QD sensitized photocatalyst was deposited on a glass slide and placed inside a custom-built photocatalysis cell. In order to follow the photoconversion of $CO_2$ by infrared (IR) spectroscopy, the reaction cell was first evacuated to a base pressure of ~$10^{-7}$ torr and then dosed with ~3 torr $H_2O$ vapor and ~0.3 torr $CO_2$. The IR spectra of the gas in the photocatalysis cell were recorded as a function of light illumination time. A second series of experiments were conducted which used gas chromatography (GC) to detect reaction products. For these experiments, the cell was purged for 15 minutes with $CO_2$ which had been bubbled through $H_2O$. A 300 W Xe arc lamp was used as the light source, and long pass filters were used to remove UV light leaving only $\lambda > 420$ nm. A water filter and control experiments rule out the possibility of heat from the lamp bulb causing the photocatalytic process. The light intensity was 100 mW/cm$^2$ at the sample. The BET surface area of the $TiO_2$ based catalysts remains essentially constant (~50 m$^2$/g) in all of the samples, indicating that the Pt co-catalysts, CdSe nanodimensioned semiconductor sensitizers, thermal annealing steps, and hydrazine treatments do not lead to structural changes of the $TiO_2$ wide band gap semiconductor material.

Figure 2:
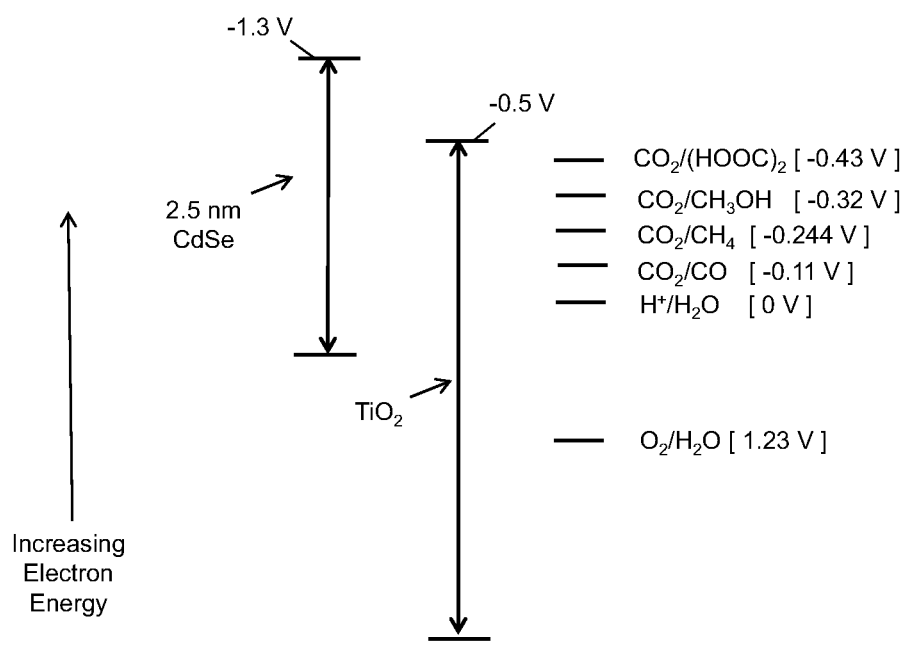
FIG. 2 shows conduction and valence bands associated with CdSe and $TiO_2$.

While the conduction band of bulk CdSe is only slightly above that of $TiO_2$, quantum confinement shifts the conduction band of CdSe QDs to higher energies which facilitates charge injection into $TiO_2$. See FIG. 2. Redox potentials indicate it is also energetically favorable for the injected electrons to initiate the reduction of $CO_2$ with $H_2O$, as illustrated at FIG. 2 FIG. 2 illustrates band energies and associated redox potentials for reactions of concern.

For efficient carrier separation across the CdSe and $TiO_2$ heterojunction, the CdSe QDs should be substantially uniformly distributed and in close/direct contact with the $TiO_2$ nanoparticles. QD uniformity may be evaluated using scanning electron microscopy (SEM) images and EDS analysis. In an exemplary t-CdSe/Pt/$TiO_2$ sample, X-ray photoelectron spectroscopy (XPS) indicated that the atomic concentrations of Pt and Cd in the sample are 0.5% and ~1%, respectively. Pt also shows multiple oxidation states with $Pt^0$ accounting for 76% of the total Pt and ~11% and ~13% for $Pt^{1+}$ and $Pt^{2+}$, respectively.

As previously discussed, good contact between the CdSe and $TiO_2$ facilitates charge transfer. Since thermal annealing can sinter QD particles, removal of QD caps with a chemical treatment is also disclosed. This can be accomplished by treating the CdSe QDs with 1 M hydrazine prior to mixing with the Pt/$TiO_2$. The hydrazine treatment is intended to remove capping molecules, allow for direct contact between the QDs and $TiO_2$, and maintain the size distribution and quality of the QDs.

Figure 3:
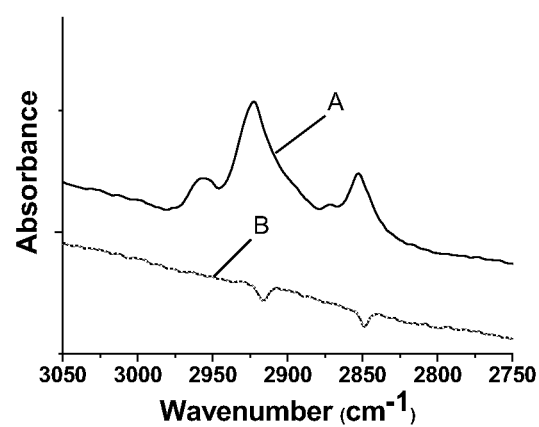
FIG. 3 shows CH stretch bands of a thin film of CdSe QDs before and after hydrazine in ethanol treatment.

The removal of the organic capping molecules on the QDs was confirmed with IR spectroscopy illustrated at FIG. 3. The size and optical properties of the CdSe QDs were preserved after the hydrazine treatment as evidenced by UV/Vis absorption spectra of the QDs, as illustrated at FIG. 4. Diffuse reflectance spectra of the c-CdSe/Pt/$TiO_2$ samples exhibit clear and distinct absorption features of CdSe QDs in the visible region, as illustrated at FIG. 5. SEM and EDS data for the c-CdSe/Pt/$TiO_2$ sample suggest that CdSe QDs form aggregates on the surface of $TiO_2$ due to the loss of the capping molecules, which limits the interfacial contact between the QDs and $TiO_2$.

The photoreduction of $CO_2$ using the t-CdSe/Pt/$TiO_2$ sample was studied with IR spectroscopy. The photocatalysts were first allowed to equilibrate in the $CO_2$/$H_2O$ atmosphere for several hours to ensure that the adsorption of gas molecules was complete. FIG. 5 shows the $CO_2$ peak area as a function of photolysis time under $\lambda > 420$ nm irradiation. After ~4 hours of reaction, the $CO_2$ peak intensity is reduced by ~10%. The reduction of the gas phase $CO_2$ absorption intensity indicates that the molecule is being consumed in a photoreaction.

To confirm that the changes in the $CO_2$ intensity result from a visible light mediated photocatalytic reaction, a series of control experiments were carried out. When the t-CdSe/Pt/TiO$_2$ sample in the cell was kept in the dark, no changes were observed in the CO$_2$ absorption intensity. For Pt/TiO$_2$ samples (no CdSe QDs present) annealed identically to the t-CdSe/Pt/TiO$_2$ samples, no CO$_2$ intensity changes are seen during irradiation with λ>420 nm light. As a final control experiment, just the CdSe QDs annealed identically to the t-CdSe/Pt/TiO$_2$ samples were exposed to the full spectral output of the lamp, as well as to visible light only (λ>420 nm), and no evidence of CO$_2$ consumption was observed. These experiments indicate that both CdSe and Pt/TiO$_2$ must be present to achieve photocatalytic activity during visible light (λ>420 nm) light excitation. The absence of activity when only Pt/TiO$_2$ or CdSe QDs are irradiated also indicates that thermally mediated processes on the surfaces of these materials are not responsible for CO$_2$ consumption. As a final note, the photocatalyst slowly deactivates over time and becomes inactive after 4 to 6 hours of illumination. See FIG. 4. The degradation may be due to the oxidation of CdSe QDs, an effect observed in similar systems. A variety of hole scavengers and caps may be suitable to improve the lifetime of the CdSe sensitized TiO$_2$ photocatalysts.

The IR experiments provide clear evidence that CO$_2$ is being consumed in a photoreaction.

To identify the products of the reaction and quantify reaction yields, gas chromatography (GC) experiments were conducted. For these experiments, the c-CdSe/Pt/TiO$_2$ samples were used to exploit the quantum confinement effect in the CdSe QDs (sizes are preserved). A mixture of 2.5 nm and 6 nm CdSe QDs were used to make the c-CdSe/Pt/TiO$_2$ samples.

After illuminating the c-CdSe/Pt/TiO$_2$ samples with visible light (λ>420 nm), methane (48 ppm g$^{-1}$ h$^{-1}$), methanol (3.3 ppm g$^{-1}$ h$^{-1}$), H$_2$ (trace), and CO (trace) were observed using the GC for detection. Only vapor phase methanol will be detected with GC sampling and liquid product will remain undetected. These conversion rates were consistent with the 10% intensity reduction seen in the IR experiments, given the different CO$_2$ partial pressures: ~0.3 torr in the IR experiments and 760 torr in the GC studies. The composition of the products also depended on the metal co-catalyst. When Fe was used in place of Pt, primarily H$_2$ production (>55 ppm g$^{-1}$ h$^{-1}$) resulted.

A series of control experiments were conducted to verify the origin of the photoactivity in the c-CdSe/Pt/TiO$_2$ samples. In order to eliminate the role of residual hydrazine in the reactions, a CO$_2$/H$_2$O filled photocatalysis cell with c-CdSe/Pt/TiO$_2$ catalyst was kept in the dark overnight and no reaction was detected. When CdSe QDs (treated identically with hydrazine) were used without Pt/TiO$_2$, no activity was observed during irradiation with the full lamp spectrum (white light) or with visible light only (λ>420 nm). Finally, if only Pt/TiO$_2$ was irradiated with λ>420 nm, no photoconversion products were detected. The results of these control experiments clearly demonstrate that the visible light activity of the CdSe/Pt/TiO$_2$ sensitized photocatalyst occurs without the direct excitation of the TiO$_2$ band gap.

The use of a hole scavenger improved the CH$_4$ production of the CdSe/TiO$_2$/Pt sensitized photocatalyst. A CdSe/TiO$_2$/Pt sample irradiated with visible light having a wavelength λ greater than 420 nm and using H$_2$O as the hydrogen source produced 32 ppm/h/g CH$_4$. Under the same conditions, except with 3 nM Na$_2$S present in the H$_2$O as a hole scavenger, 39 ppm/h/g CH$_4$ was produced.

Thus, the disclosure herein describes a sensitized photocatalyst capable of catalyzing the photoreduction of CO$_2$ using visible light illumination (λ>420 nm) only. The photocatalytic reduction of CO$_2$ may use readily available sunlight to convert CO$_2$ into valuable chemicals, such as methanol or methane, in a carbon friendly manner. The sensitized photocatalyst is comprised of a wide band gap semiconductor material in contact with a semiconductor sensitizer, and a transition metal co-catalyst loaded on the wide band gap semiconductor material. In order to affect photocatalytic reduction of CO$_2$ using visible light, the semiconductor sensitizer has a band gap such that visible light is absorbed and photoexcitation in the semiconductor sensitizer results, driving electrons in the semiconductor from the valence band to the conduction band. The conduction band of the semiconductor sensitizer has a more negative potential than the redox potential of CO$_2$, and semiconductor sensitizer and the wide band gap semiconductor material form a Type II band alignment, where the conduction band of the semiconductor sensitizer has a more negative potential than the conduction band of the wide band gap semiconductor material. The sensitized photocatalyst catalyzes the photoreduction of CO$_2$ in the presence of hydrogen to produce products such as CH$_4$, CH$_3$OH, H$_2$, CO, and other hydrocarbons.

Accordingly, the method provides a method of photocatalytically reducing CO$_2$ under visible light excitation in the presence of hydrogen from a hydrogen source utilizing a sensitized photocatalyst comprised of a wide band gap semiconductor, a transition metal co-catalyst, and a semiconductor sensitizer.

Further, the method provides for photocatalytically reducing CO$_2$ under visible light excitation in the presence of hydrogen from a hydrogen source in order to produce product molecules such as hydrocarbons, H$_2$, and others.

Further, the method provides for controlling the composition of the product molecules based on the transition metal co-catalyst.

Further, the method provides a method of photocatalytically reducing CO$_2$ utilizing a sensitized photocatalyst comprised of particles of the wide band gap semiconductor, the transition metal co-catalyst, and the semiconductor sensitizer, in order to optimize charge injection and band alignments under visible light illumination.

Further, the method provides for photocatalytically reducing CO$_2$ under visible light illumination utilizing a sensitized photocatalyst in a CO$_2$ and H$_2$O environment.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

What is claimed is:

1. A method of photocatalytically reducing $CO_2$ in the presence of water comprising:
   producing a sensitized photocatalyst comprised of:
   a wide band gap semiconductor material, where the valence band of the wide band gap semiconductor material has a more positive potential than the redox potential of $H_2O$,
   a semiconductor sensitizer loaded on a surface of the wide band gap semiconductor material, where the semiconductor sensitizer comprises a binary semiconductor, where the binary semiconductor is InP, GaAs, PbS, PbSe, ZnTe, CdS, CdSe, or CdTe, such that the binary semiconductor has a band gap such that visible light produces photoexcitation in the binary semiconductor, and where the valence band of the wide band gap semiconductor material has a more positive potential than the redox potential of $H_2O$, and where the binary semiconductor has a band gap such that the binary semiconductor and the wide band gap semiconductor material form a heterojunction at an interface between the binary semiconductor and the wide band gap semiconductor material, where the heterojunction has a type II band alignment, and where the conduction band of the binary semiconductor has a more negative potential than the conduction band of the wide band gap semiconductor material,
   a co-catalyst loaded on the wide band gap semiconductor material, where the co-catalyst is comprised of a transition metal;
   and exposing the sensitized photocatalyst to $CO_2$ and $H_2O$, and exposing the sensitized photocatalyst to a visible light illumination, such that some portion of the $CO_2$ is photocatalytically reduced and such that product molecules are produced.

2. The method of claim 1 where the co-catalyst is selected based on the composition of the product molecules.

3. The method of claim 2 where the co-catalyst is Pt and the product molecules are hydrocarbons.

4. The method of claim 2 where the co-catalyst is Fe and the product molecules are diatomic hydrogen.

5. The method of claim 2 where the binary semiconductor is a semiconductor having a direct band gap.

6. The method of claim 5 where the where the wide band gap semiconductor material is $TiO_2$ or ZnO.

7. The method of claim 6 where the co-catalyst is Pt, the binary semiconductor is CdSe, and the product molecules are hydrocarbons.

8. The method of claim 6 where the co-catalyst is Fe, the binary semiconductor is CdSe, and the product molecules are $H_2$.

9. The method of claim 1 where the wide band gap semiconductor material is $TiO_2$, the co-catalyst is Pt, the binary semiconductor is CdSe, and the product molecules are hydrocarbons.

10. The method of claim 1 where the wide band gap semiconductor material is $TiO_2$, the co-catalyst is Fe, the binary semiconductor is CdSe, and the product molecules are $H_2$.

11. The method of claim 1 where the wide band gap semiconductor material is $TiO_2$ or ZnO.

12. The method of claim 1 where the wide band gap semiconductor material is comprised of a plurality of semiconductor particles, and where the co-catalyst is comprised of a plurality of co-catalyst particles, and where the co-catalyst is loaded on the wide band gap semiconductor when at least one of the co-catalyst particles is loaded on at least one of the semiconductor particles to form a catalyzed particle, and where the semiconductor sensitizer is comprised of a plurality of sensitizing particles, and where the semiconductor sensitizer contacts the wide band gap semiconductor material when at least one of the sensitizing particles contacts the catalyzed particle.

13. The method of claim 12 where charge injection occurs from the semiconductor sensitizer to the wide band gap semiconductor material when the sensitized photocatalyst is exposed to the visible light illumination, and where the at least one of the sensitizing particles has a sensitizing particle diameter and the sensitizing particle diameter is selected based on a desired rate of charge injection, and where the at least one of the semiconductor particles has a semiconductor particle diameter and the semiconductor particle diameter is selected based on a desired rate of charge injection.

14. The method of claim 12 where the at least one of the sensitizing particles has a sensitizing particle diameter and the sensitizing particle diameter is less than 10 nm and where the at least one of the semiconductor particles has a semiconductor particle diameter and the semiconductor particle diameter is less than 50 nm.

15. The method of claim 12 where the at least one of the sensitizing particles has a sensitizing particle diameter and the sensitizing particle diameter is selected in order to produce a desired band gap of the at least one of the sensitizing particles.

16. The method of claim 12 where a diameter of a at least one of the sensitizing particles is less than 50 nm and where a diameter of the at least one of the semiconductor particles particle is less than 100 nm.

* * * * *